(12) United States Patent
Baker et al.

(10) Patent No.: US 9,125,800 B2
(45) Date of Patent: Sep. 8, 2015

(54) STOMA LENGTH INDICATOR ASSEMBLY AND POSITIONING SYSTEM

(75) Inventors: Andrew T. Baker, Norcross, GA (US); Jennifer S. Stadelman, Alpharetta, GA (US); Dwayne J-K Jackson, Atlanta, GA (US); Sridhar Ranganathan, Suwanee, GA (US); Phillip A. Schorr, Cumming, GA (US); James M. Takeuchi, Woodstock, GA (US)

(73) Assignee: AVENT, INC., Alpharetta, GA (US)

( * ) Notice: Subject to any disclaimer, the term of this patent is extended or adjusted under 35 U.S.C. 154(b) by 538 days.

(21) Appl. No.: 13/245,552

(22) Filed: Sep. 26, 2011

(65) Prior Publication Data

US 2012/0078167 A1    Mar. 29, 2012

Related U.S. Application Data

(60) Provisional application No. 61/386,793, filed on Sep. 27, 2010, provisional application No. 61/446,229, filed on Feb. 24, 2011.

(51) Int. Cl.

| A61J 15/00 | (2006.01) |
|---|---|
| A61B 17/34 | (2006.01) |
| A61M 25/10 | (2013.01) |
| A61M 29/02 | (2006.01) |

(52) U.S. Cl.
CPC ......... *A61J 15/0015* (2013.01); *A61B 17/3415* (2013.01); *A61M 25/1002* (2013.01); *A61M 29/02* (2013.01)

(58) Field of Classification Search
CPC .............. A61J 15/0015; A61J 15/0026; A61J 15/0034; A61J 15/0053; A61J 15/0061; A61J 15/0069; A61J 15/0038; A61J 15/0042; A61B 17/3415
USPC ............. 604/117, 164.04, 174, 175, 285, 910
See application file for complete search history.

(56) References Cited

U.S. PATENT DOCUMENTS

| 4,972,845 | A |  | 11/1990 | Iversen et al. |
|---|---|---|---|---|
| 5,092,850 | A |  | 3/1992 | Buma |
| 5,413,565 | A |  | 5/1995 | Michels et al. |
| 5,484,420 | A |  | 1/1996 | Russo |
| 5,860,952 | A |  | 1/1999 | Quinn |
| 5,891,113 | A | * | 4/1999 | Quinn ........................... 604/526 |

(Continued)

FOREIGN PATENT DOCUMENTS

| EP | 0 615 740 A1 | 9/1994 |
|---|---|---|
| WO | WO 93/08729 A1 | 5/1993 |

(Continued)

*Primary Examiner* — Kami A Bosworth
(74) *Attorney, Agent, or Firm* — Dority & Manning, PA

(57) ABSTRACT

An indicator assembly for use with a non-vascular catheter device. The indicator assembly includes: a first retainer secured to a catheter tube, the first retainer being an indwelling retainer which is deployed within a non-vascular lumen or cavity of the body; a second retainer secured to the catheter tube, the second retainer deployed outside the human body; and an indicator located outside the body on the catheter tube between the first retainer and the second retainer. The first retainer and the second retainer are configured to maintain substantially the same position with respect to each other on the tube and the indicator is configured to signal a change in position with respect to either the first or the second retainer, thereby indicating a change in the length of a stoma.

18 Claims, 12 Drawing Sheets

(56) References Cited

U.S. PATENT DOCUMENTS

| | | |
|---|---|---|
| 6,030,361 A | 2/2000 | Miyashiro |
| 6,231,547 B1 | 5/2001 | O'Hara |
| 6,231,549 B1 | 5/2001 | Noecker et al. |
| 6,494,848 B1 | 12/2002 | Sommercorn et al. |
| 6,666,853 B2 | 12/2003 | Chu et al. |
| 6,764,453 B2 | 7/2004 | Meier |
| 7,582,072 B2 | 9/2009 | McMichael |
| 7,648,479 B2 | 1/2010 | Solovay et al. |
| 2003/0212349 A1 | 11/2003 | Meier |
| 2004/0116868 A1* | 6/2004 | Forman et al. ............... 604/174 |
| 2007/0005086 A1* | 1/2007 | Gresham ..................... 606/167 |
| 2008/0091146 A1 | 4/2008 | Solovay et al. |
| 2010/0057013 A1 | 3/2010 | Harada |
| 2011/0009828 A1* | 1/2011 | Prechtel et al. ............... 604/175 |

FOREIGN PATENT DOCUMENTS

| | | |
|---|---|---|
| WO | WO 2008/005496 A2 | 1/2008 |
| WO | WO 2008/019082 A2 | 2/2008 |
| WO | WO 2008/027375 A2 | 3/2008 |
| WO | WO 2008/157172 A1 | 12/2008 |
| WO | WO 2009/155537 A1 | 12/2009 |
| WO | WO 2010/115102 A1 | 10/2010 |

* cited by examiner

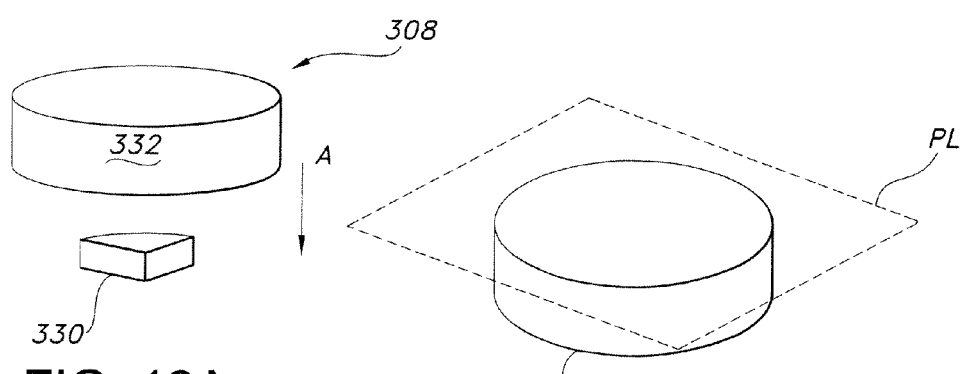
FIG. 12A
FIG. 12B
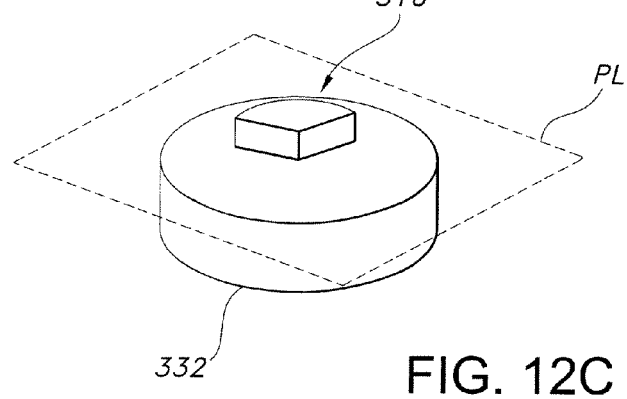
FIG. 12C

STOMA LENGTH INDICATOR ASSEMBLY AND POSITIONING SYSTEM

This application claims the benefit of priority from U.S. Provisional Application No. 61/386,793 filed on Sep. 27, 2010 and U.S. Provisional Application No. 61/446,229 filed on Feb. 24, 2011, the contents of which are incorporated herein by reference.

FIELD OF THE INVENTION

The present invention relates to catheters or feeding tubes and their placement in the body of a patient.

BACKGROUND

Numerous situations exist in which interior parts of the human body needs to be catheterized through an artificial stoma to achieve a desired medical goal. Relatively common situations are for drainage of retained fluids and administering nutritional solutions or medicines directly into the stomach or intestines. For these situations a stoma is formed percutaneously and an indwelling device is placed through the stoma. By way of example the surgical opening and/or the procedure to create a stoma spanning between the stomach or intestinal wall and the exterior of the skin is commonly referred to as "gastrostomy". A device with a catheter component, e.g. a feed tube, placed through such a stoma allows injection of feeding solutions through the tube to provide nutrients directly to the stomach or intestines (known as enteral feeding). A variety of different devices intended for enteral feeding have been developed over the years, including some having a "low profile" relative to that portion which sits on a patient's skin, as well as those having the more traditional or non-low profile configuration. These percutaneous transconduit devices (sometimes referred to as "percutaneous transconduit catheters") are frequently referred to as "gastrostomy tubes", "percutaneous gastrostomy tubes", "PEG tubes" or "enteral feeding tubes". U.S. Pat. No. 6,019,746 for a "Low Profile Balloon Feeding Device" issued to Picha et al. on Feb. 1, 2000, provides an example of one device.

Such devices have a head portion (sometimes referred to as a "base") that resides outside of the patient and sits on the patient's skin. To prevent the device from being pulled out of the stoma, various types of retainers are used at a distal end of the device and reside inside the patient. Examples of conventional devices with Malecot tips or similar expanding tips as retainers are found at, for example, U.S. Pat. No. 3,915,171 for "Gastrostomy Tube" issued to Shermeta; U.S. Pat. No. 4,315,513 for "Gastrostomy and Other Percutaneous Transport Tubes" issued to Nawash et al.; U.S. Pat. No. 4,944,732 for "Gastrostomy Port" issued to Russo; and U.S. Pat. No. 5,484,420 for "Retention Bolsters for Percutaneous Catheters" issued to Russo. Exemplary commercial products with head portions and retainer portions include the Passport® Low Profile Gastrostomy Device available from Cook Medical, Inc. of Bloomington, Ind. and the Mini One™ Non-Balloon Button available from Applied Medical Technology, Inc. of Brecksville, Ohio.

One frequent problem with these devices is that during initial placement, the physician may be too aggressive in applying pressure when seating the retainer. This will result in the distance between the head and the retainer being too short for the length of the stoma. As a result, the stoma tract will be squeezed between the head and the retainer causing discomfort and pain for the patient.

Another frequent problem with these devices is that the length of the stoma tract itself may change over time due to feeding and nutrition uptake. For example, weight gain by a patient may result in an increase in the thickness of tissue between the head and retainer. This additional tissue can push axially against the head and the retainer causing discomfort and pain for the patient. Alternatively and/or additionally, inflammation or infection of tissue around the stoma site may cause swelling between the head and the retainer of the tube. The swelling tissue can push axially against the head and the retainer causing discomfort and pain for the patient. On the other hand, weight loss by a patient may result in a decrease in the thickness of tissue between the head and retainer and, after a proper initial placement, cause the head and the retainer to fit too loosely causing leakage or movement of the device.

Accordingly, there is a need for an indicator assembly for devices with catheter, head and retainer components that can signal changes in the axial length of the stoma tract. There is also a need for an indwelling catheter device that incorporates such indicator assembly. A need also exists for an initial positioning system that can provide a signal to a physician that the proper axial length of the retention system of an indwelling catheter device has been reached. There is a need for a repositionable indicator system that provides a signal indicating proper axial positioning of the retention system of an indwelling catheter device (e.g. an enteral feeding tube or other catheter tube).

SUMMARY

In response to the difficulties and problems discussed herein, the present invention provides an indicator assembly for use with an in-dwelling non-vascular device having a base deployed outside the human body and an indwelling retainer which is deployed within a lumen or cavity of the body by insertion through a stoma. The indicator assembly includes: a first retainer secured to a catheter tube, the first retainer being an indwelling retainer which is deployed within a non-vascular lumen or cavity of the body; a second retainer secured to the catheter tube, the second retainer deployed outside the human body; and an indicator located outside the body on the catheter tube between the first retainer and the second retainer.

According to the invention, the first retainer and the second retainer are configured to maintain substantially the same position with respect to each other on the catheter tube and the indicator is configured to signal a change in position with respect to either the first or the second retainer, thereby indicating a change in the length of a stoma.

The first retainer is configured to be positioned in a nonvascular lumen or cavity of a patient (e.g., a gastric lumen, jejunum, peritoneal cavity or the like). The indicator is configured to be positioned externally near the surface of the skin of the patient and the second retainer is configured to be generally above the indicator. The second retainer may be releasably secured to the tube such that the location of second retainer on the tube may be changed.

In an aspect of the invention, the indicator may include at least a first indicator element and a second indicator element. At least one of the indicator elements (e.g., the first indicator element, the second indicator element or additional indicator element(s), if present) may be configured to be movable and/or deformable with respect to the other to provide a signal. The signal provided by the indicator is desirably a visual signal. The signal may also be a tactile signal or a combination of visual and tactile signals. One or more of the indicator elements may be affixed to the tube and may serves as the second retainer. The non-vascular catheter tube may be an enteral feeding tube, a jejunal feeding tube, a peritoneal drainage tube or the like.

The present invention also encompasses an indicator assembly for use with a non-vascular catheter device having a base deployed outside the human body and an indwelling retainer which is deployed within a lumen (i.e., a non-vascular lumen or non-vascular cavity) of the body by insertion through a stoma, such indicator assembly including: a first retainer secured to a catheter tube, the first retainer being an indwelling retainer which is deployed within a lumen of the body; and an indicator secured to the catheter tube such that it is deployed outside the human body, the indicator having at least a first indicator element and a second indicator element, such that the first retainer and an indicator element are configured to maintain substantially the same position with respect to each other on the tube and one of the indicator elements is configured to be movable and/or deformable with respect to the other the element so the indicator is configured to signal a change in position with respect to the first retainer, thereby signaling a change in the length of a stoma. According to the invention, the non-vascular catheter device may be an enteral feeding tube, a jejunal feeding tube, a peritoneal drainage tube or the like.

The present invention also encompasses a positioning system for a retainer of a non-vascular catheter device having a base deployed outside the human body and an indwelling retainer which is deployed within a non-vascular lumen or cavity of the body by insertion through a stoma. The positioning system includes: a first retainer fixedly attached to a catheter tube, the first retainer being an indwelling retainer for deployment within a non-vascular lumen or cavity of the body; a second retainer releasably secured to the tube such that the location of second retainer on the tube may be changed; and an indicator located on the tube between the first retainer and the second retainer, the indicator being deployed at a surface of the skin of the patient to provide a placement signal (e.g., a visual signal and/or a tactile signal), such that advancement of the second retainer toward the first retainer generates a placement signal and then retraction of the second retainer away from the first retainer until it no longer generates a placement signal provides a placement position for the second retainer such that the second retainer may be releasably secured to the tube. According to the invention, the non-vascular catheter device may be an enteral feeding tube, a jejunal feeding tube, a peritoneal drainage tube or the like.

Another aspect of the invention encompasses a repositionable indicator system for a non-vascular catheter device having a base deployed outside the human body and an indwelling retainer which is deployed within a lumen of the body by insertion through a stoma. The repositionable indicator system includes: an external retainer incorporating a releasable lock to releasably secure the retainer on a catheter tube outside the human body; and an indicator located on the tube, the indicator configured to be positioned between the skin of a patient and the retainer such that the indicator provides a signal (e.g., a visual and/or tactile signal) in response to a force applied to the indicator between the skin and the external retainer. According to the invention, the non-vascular catheter device may be an enteral feeding tube, a jejunal feeding tube, a peritoneal drainage tube or the like.

Yet another aspect of the invention encompasses a method for positioning an external retainer of a non-vascular catheter device having a catheter tube, a base deployed outside the human body and an indwelling retainer which is deployed within a non-vascular lumen or cavity of the body by insertion through a stoma. The method includes the steps of: (a) inserting a portion of a catheter tube incorporating the indicator assembly as generally described above through a stoma to deploy a first retainer within a non-vascular lumen or cavity of the body, for example, a gastric lumen; (b) advancing a second retainer, releasably securable to the tube and deployed outside the human body, towards the first retainer until an indicator deployed at a surface of the skin of the patient provides a placement signal (e.g., a visual and/or tactile signal); (c) retracting the second retainer away from the first retainer until the indicator no longer provides a placement signal; and (d) releasably securing the second retainer to the tube. According to the invention, the non-vascular catheter device may be an enteral feeding tube, a jejunal feeding tube, a peritoneal drainage tube or the like.

A better understanding of the above and many other features and advantages of the indicator assembly for use with an in-dwelling non-vascular device may be obtained from a consideration of the detailed description of the invention below, particularly if such consideration is made in conjunction with the appended drawings.

BRIEF DESCRIPTION OF THE DRAWINGS

FIGS. 12A to 12C are perspective view illustrations of a detail of an exemplary image block from an exemplary stoma length indicator assembly.

DETAILED DESCRIPTION

Figure 1:
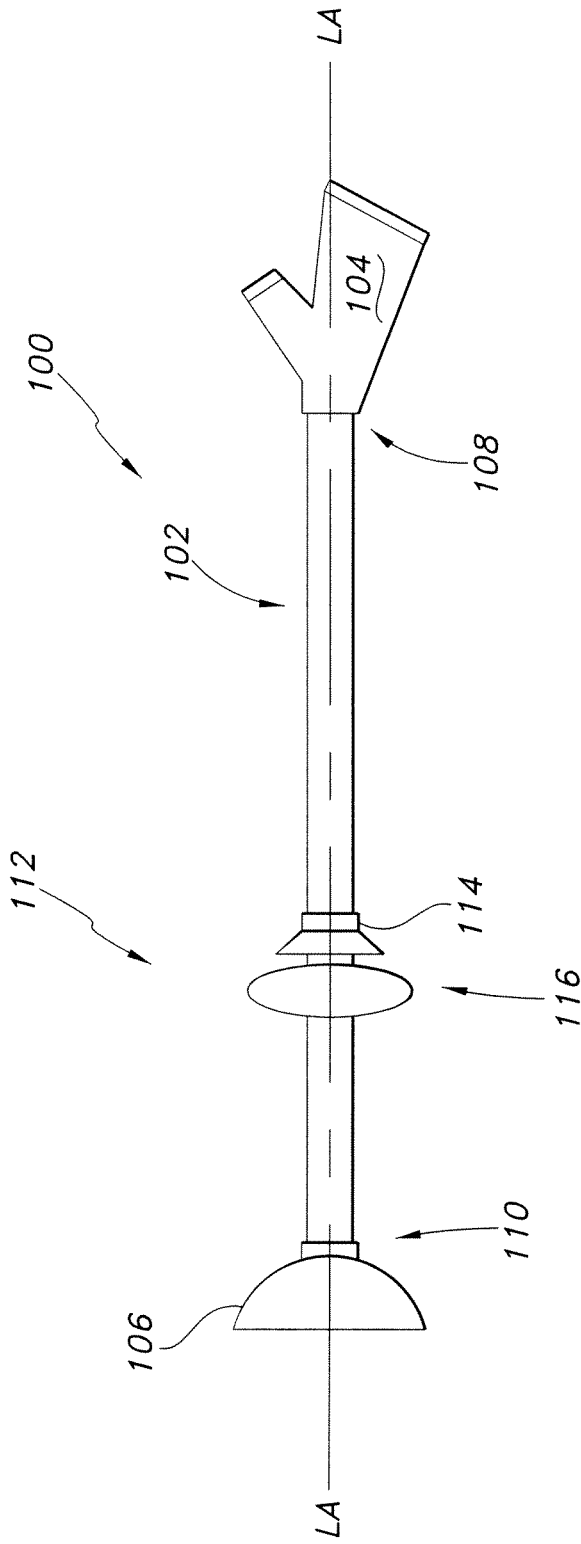
FIG. 1 is a side view illustrating an exemplary enteral feeding tube or "PEG" incorporating an exemplary stoma length indicator assembly.

Reference will now be made in detail to one or more embodiments, examples of which are illustrated in the drawings. It should be understood that features illustrated or described as part of one embodiment may be used with another embodiment to yield still a further embodiment.

The present invention relates to an indicator assembly for use with a non-vascular catheter device (e.g. enteral feeding tube, jejunal feeding tube, peritoneal drainage tube, and the like) having a catheter tube, an external retainer (e.g. base deployed outside the human body) and an indwelling retainer which is deployed within a lumen (i.e., a non-vascular lumen or cavity of the body such as, for example, a gastric lumen, jejunum, peritoneal cavity or the like) of the body by insertion through a stoma, and an indicator. The insertion through the stoma may be from outside the body or it may be performed from inside the body using endoscopic techniques. In this context, the term "insertion" should be understood as putting in or introducing the catheter tube in place in a stoma so that the base is deployed outside the human body and the indwelling retainer is deployed within a non-vascular lumen or cavity. Generally speaking, the indicator assembly affixed to the exterior of a catheter device (i.e., an enteral feeding tube such as, for example a configurable PEG or "C-PEG" device) and in such configuration, the indicator would be affixed on the skin contacting portion of the C-PEG device.

The indicator assembly is a mechanical assembly. That is, it is non-electronic or non-electrical. This ensures simple, reliable operation without the need for batteries complex circuitry, output displays or the like. The indicator assembly ensures that the catheter device (e.g., the PEG) does not slide deeper into the patient in the same way that catheter device retention mechanisms (e.g., the PEG's indwelling retainer component) prevent catheter devices from being pulled out of the patient. The indicator assembly allows the catheter device tubing to reversibly interlock with it. In some embodiments, the tubing may lock into the indicator assembly and form a 90 degree bend. The indicator assembly has the ability to be used with a variety of catheter device such as enteral feeding tubes or PEG devices with specific tubing diameters and is not limited to only being used in conjunction with a particular catheter device.

The indicator assembly provides a discrete visual signal (or in some cases, a discrete tactile signal) about the pressure or force drawing the retainers towards the stoma tract. That is, the indicator assembly responds to the pressure generated on the compression of the tissue between the retainer portions of the catheter device. If the catheter device (e.g., enteral feeding tube or other PEG device) encounters a specific pressure (e.g., during an aggressive placement or caused either by manual tightening or through normal growth of the tissue) the indicator assembly provides a discrete visual signal that the pressure or force drawing the retainers toward the stoma tract is different from a predetermined pressure such as, for example, a pressure that is sufficient to deform or collapse the indicator assembly.

Referring now to FIG. 1 of the drawings, there is shown a side view illustration of an exemplary non-vascular catheter device. For purposes of this description, the non-vascular catheter device will be referred to as an enteral feeding tube 100 (which may also be referred to as a "PEG" device) composed of a flexible tube 102 (which may also be referred to as a "catheter" or "shaft") having walls defining at least one lumen therethrough. The PEG device 100 also has a base 104 deployed outside the human body and an indwelling retainer 106 (also referred to as "a first retainer" 106) which is deployed within a non-vascular lumen or cavity of the body (e.g., a gastric lumen). The first retainer 106 may be a conventional molded flexible retainer or it may be a configurable retainer that changes from an "insertion" or "removal" state in which the retainer has a diameter that is generally about the same as the tube portion of the PEG device to an expanded "retention" or "deployed" state in which the retainer takes on an expanded mushroom or dome-shape that has a substantially larger diameter than the tube portion of the device. Such configurable PEG devices may be referred to as C-PEG devices.

Generally speaking, the base 104 of the enteral feeding tube 100 has one or more openings allowing access to the lumen(s) of the flexible tube 102 through the base. The flexible tube 102 has a proximal end 108 and a distal end 110, a longitudinal axis "LA", a width and a length. The flexible tube 102 is desirably positioned through the base 104 in communication with the one or more openings in the base. The walls of the flexible tube 102 define one or more lumens from the opening(s) in the base to the distal end of the catheter which desirably are in communication with an opening or openings in the first retainer 106.

An indicator assembly 112 is located on the flexible tube 102. The assembly 112 includes the indwelling or first retainer 106. This first retainer 106 is secured away from a proximal end 108 of the flexible tube 102 of the enteral feeding tube 100. FIG. 1 depicts the first retainer 106 at the distal end 110 of the tube 102; however the first retainer 106 can be positioned on tube 102 proximally from the distal end 110. As noted above, the first retainer 106 is deployed within a non-vascular lumen or cavity of the body. The indicator assembly 112 may also include a second retainer 114 secured on the flexible tube 102 proximal to the first retainer 106. This second retainer 114 (if present) is deployed outside the human body. An indicator 116 is also located on the flexible tube 102 and is configured to be part of the enteral feeding tube 100 that is located outside the body (i.e., against the skin of a patient) between the first retainer 106 and the second retainer 114. According to an aspect of the invention, a portion of the indicator 116 may be configured to serve as the second retainer 114 as will be discussed later.

Figure 2:
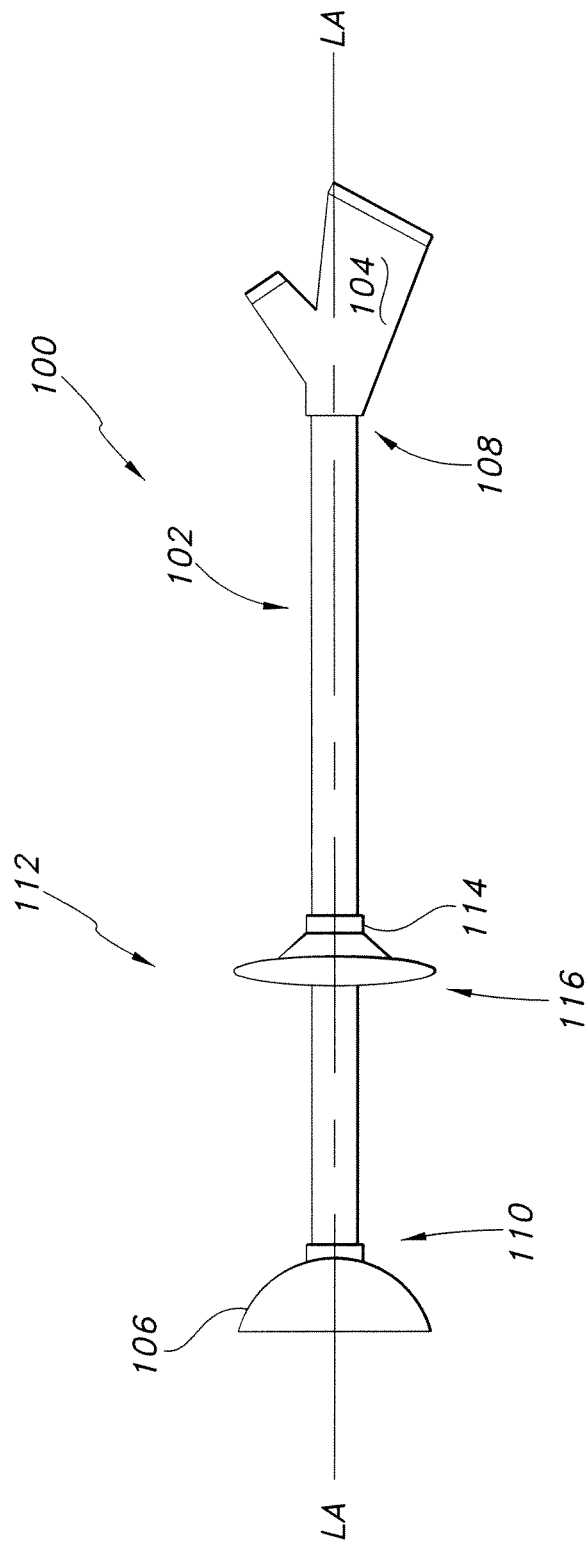
FIG. 2 is a side view illustrating an exemplary enteral feeding tube or "PEG" incorporating an exemplary stoma length indicator assembly in a compressed configuration.

As show in FIG. 2, the first retainer 106 and the second retainer 114 are configured to maintain substantially the same position with respect to each other on the flexible tube 102 and the indicator 116 is configured to signal a change in position with respect to either the first retainer 106 or the second retainer 114, thereby indicating a change in the length of a stoma. In FIG. 2, the indicator 116 is illustrated under an axial pressure caused by an increase in the length of a stoma (not illustrated) that may result from swelling around the stoma site, infection, weight gain or the like that deforms at least a portion of the indicator. For example, the indicator may flatten and/or expand in a radial direction. As generally illustrated in FIGS. 1 and 2, the indicator 116 may be configured to be positioned at a surface of the skin of the patient and the second retainer 114 may be configured to be positioned above the indicator. In an aspect of the invention, the second retainer 114 may be releasably secured to the tube 102 such that the location of second retainer 114 on the tube may be changed.

Figure 3:
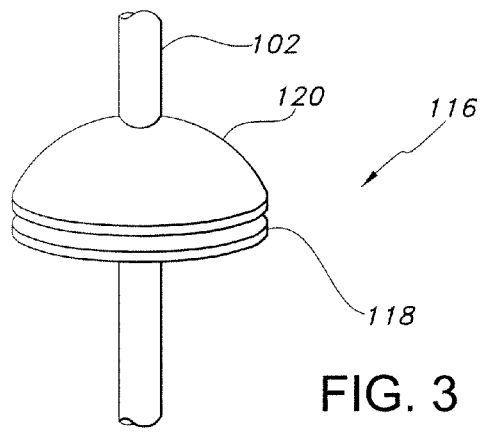
FIG. 3 is a side perspective view illustrating an exemplary stoma length indicator assembly.

Referring now to FIG. 3, there is shown in side perspective view an exemplary indicator 116 that may include at least a first indicator element 118 and a second indicator element 120. At least one of the indicator elements 118, 120 may be configured to be movable and/or deformable with respect to the other to provide a signal. The signal provided by the indicator is desirably a visual signal. When indicator element 120 is affixed to the tube 102 it may serve as the second retainer 114.

Exemplary indicators 116 are illustrated in FIGS. 4-14. Generally speaking, the indicator 116 may include a first indicator element 118 (e.g., a generally flat disc or donut shaped element) adjacent the skin of the wearer and a second indicator element 120 located proximally above the first indicator element 118 (i.e., located in a direction oriented away from the body in the direction of the base 104). The two indicator elements are configured to be movable with respect to each other and the second element 120 may be affixed to the catheter or tube component 102 of an enteral feeding device 100 as shown in FIGS. 1 and 2. For example, the second indicator element 120 may be releasably affixed to the flexible feeding tube component 102 and the first indicator element 118 may be configured to deform or move relative to the second element 120. When the pressure between the second indicator element 120 (which may be a base of a PEG device such as, for example, the base of a low-profile feeding tube device) and the first indicator element 118 exceeds a threshold amount, the first element 118 and the second element 120 move relative to each other. This movement results in a change that provides a visual signal—which can be interpreted by the user or caretaker as a change in pressure.

Figures 4A, 4B:
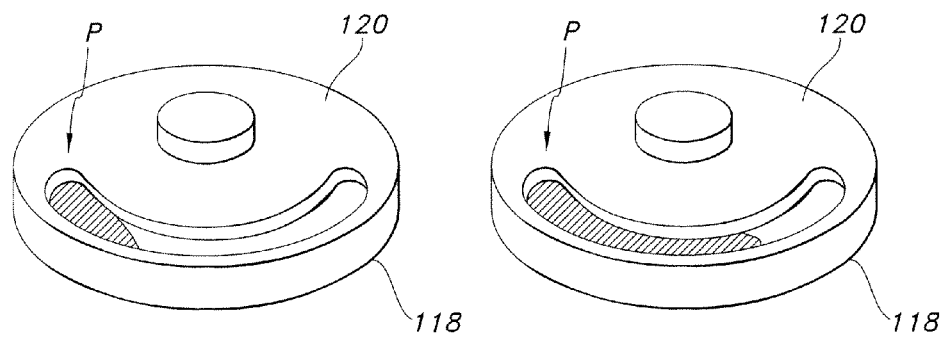
FIGS. 4A and 4B are a side perspective view illustrations showing a detail of an exemplary stoma length indicator assembly.

For example, FIGS. 4A and 4B illustrate how a first indicator element 118 that incorporates at least one disc or other internal component that rotates in response to pressure applied in an axial direction (i.e., along the longitudinal axis LA), with respect to a second indicator element 120 revealing a change in color or pattern to generate a signal indicating a change in the length of a stoma. The first indicator element 118 may incorporate springs or other conventional components (not shown) that translate movement in an axial direction into rotation of an internal component such as a disc. Different patterns and color combinations may be used to improve the signal contrast. In a first position, a first color or pattern "P" is visible (or the absence of a first color or pattern) and in a second position that is present in response to a change in pressure resulting from a change in the axial dimensions (e.g., length) of a stoma, more of the first color or pattern "P", or a second color or pattern is visible (or the absence of a first color or pattern). As another example, a first indicator element 118 (e.g., in the form of blinds or a lattice-like structure) may fold or collapse with respect to the second indicator element 120 in response to pressure to signal incremental changes in pressure. Such folding or collapse of the first indicator element 118 can provide a change in pattern or color to generate a signal indicating a change in the length of a stoma.

In an aspect of the invention, elastic components may be used between the first and second indicator elements 118, 120 (e.g., inside a base and top) to provide a restorative rotational force. The second indicator element 120 (located in the proximal direction above the first indicator element 118) may rotate relative to the first indicator element 118 to introduce or expose a color and/or pattern "P", open and/or close a window, or remove or hide a color and/or panel "P". The amount and ease of rotation is dependent on the amount of force applied to the first indictor element 118. Such a configuration may be used to indicate a removal or absence of pressure against the indicator that may be caused by partial or complete deflation of a balloon retainer, weight loss, and/or reduction in swelling and/or inflammation of a stoma site.

Figure 5A:
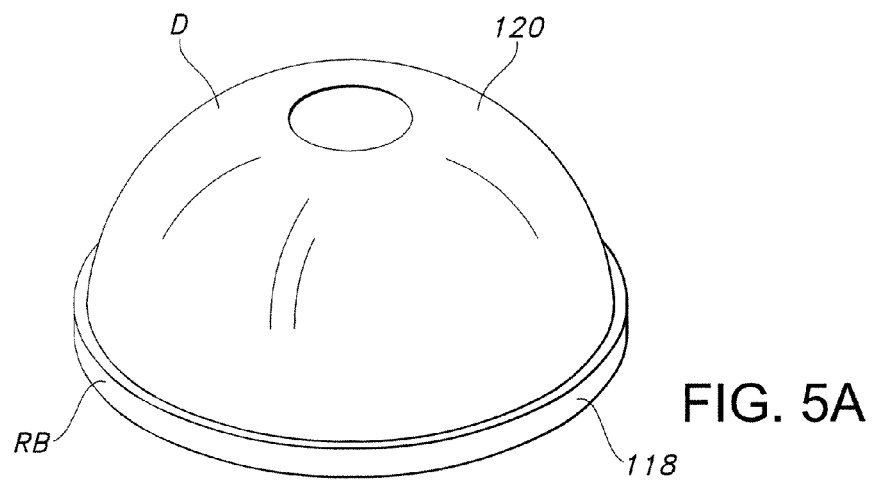
FIGS. 5A and 5B are a perspective view illustrations showing a detail of another exemplary stoma length indicator assembly.
Figure 5B:
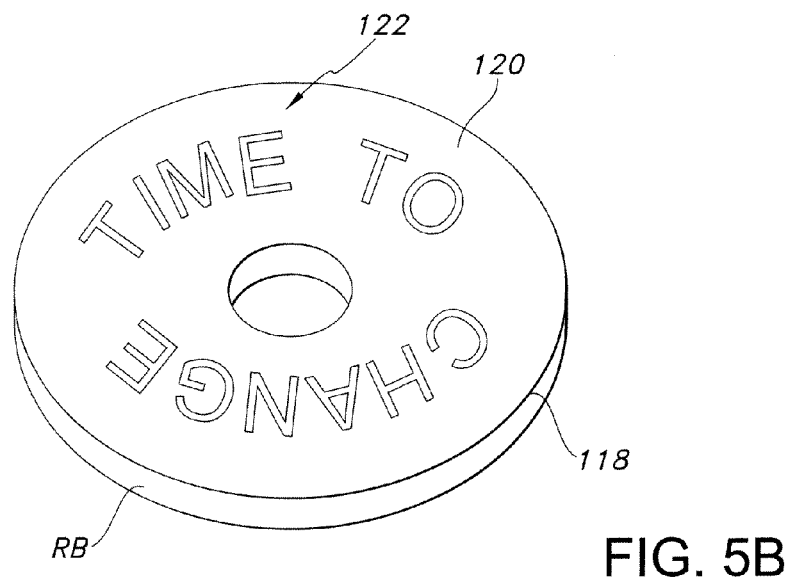

FIGS. 5A and 5B illustrate an indicator having a second indicator element 120 in the form of a flexible dome top "D" which may be formed of flexible translucent polymers including but not limited to silicones, PVCs (poly-vinyl chloride) or urethanes and a first indicator element 118 in the form of a base "RB" that is relatively much more rigid than the flexible dome top. The second indicator element 120 (e.g., the dome) is affixed, secured or joined to the flexible tube 102 of an enteral feeding tube device 100 (e.g., the second indicator element 120 may be friction fitted to the tube 102 or secured using other conventional techniques). When first indicator element 118 is pushed toward the second indicator element 120 (e.g., by swelling of the stoma site which increases the length of the stoma site), the first indicator element 118 (e.g., the base) is pushed against the second indicator element 120 (e.g., the dome top) and the dome collapses to reveal color or other visual cue 122 that becomes visible through the second indicator element 120 thereby signaling a change in stoma length and/or pressure against the indicator. For example, the flexible dome may be composed of a translucent material. Under compression, the dome collapses to reveal a visual signal 122 located on an inner, bottom surface. The signal could consist of or include a variety of graphics, colors, patterns, and messages.

Figure 6A:
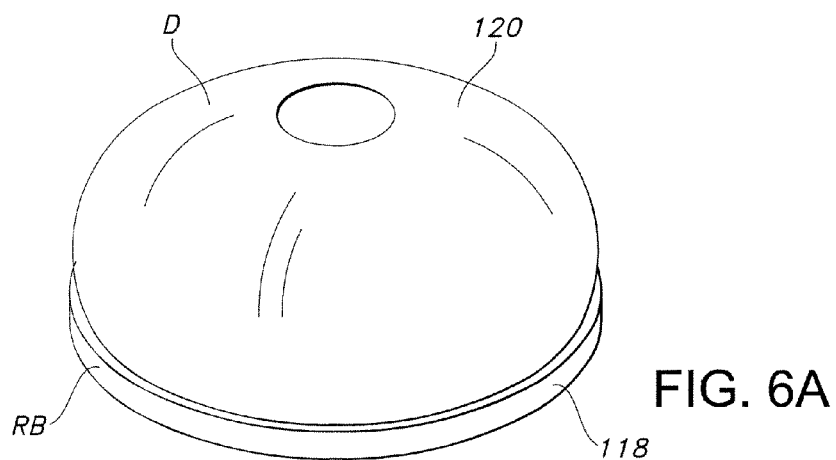
FIGS. 6A and 6B are a perspective view illustrations showing a detail of another exemplary stoma length indicator assembly.
Figure 6B:
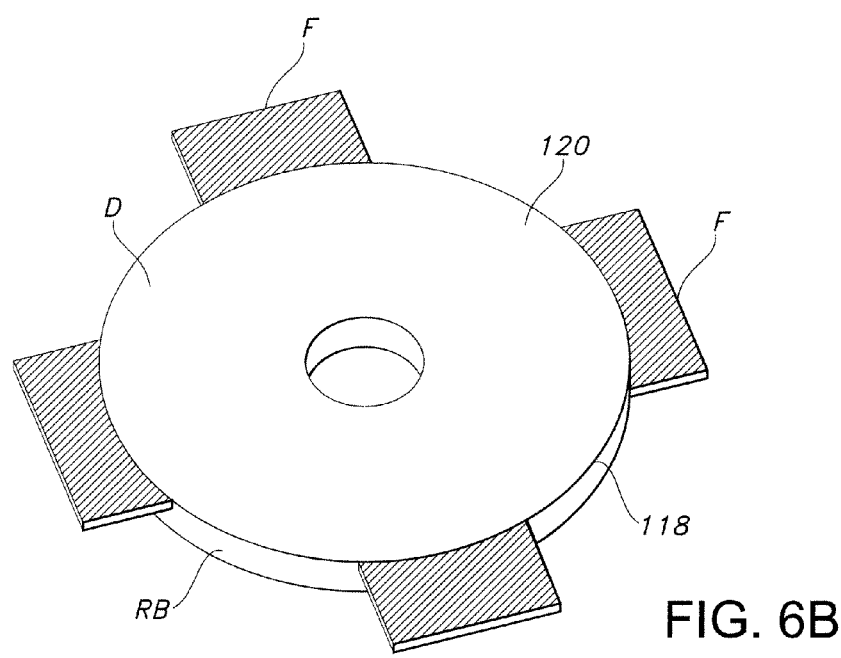

FIGS. 6A and 6B illustrate an indicator 116 having a second indicator element 120 in the form of a flexible dome top "D" and first indicator element 118 in the form of a rigid base "RB". The second indicator element 120 (e.g., the dome) is affixed, secured or joined to the flexible tube 102 of an enteral feeding tube device 100. When the stoma tract increases in length, the second indicator element 120 (e.g., the dome) and the first indicator element 118 (e.g., the base) move closer together. In response to this movement, the second indicator element 120 (e.g., the dome) collapses pushing visual flags "F" or other indicia out the sides of the device.

Referring now to FIGS. 7A to 7D, other exemplary embodiments of an indicator 116 may provide a "disappearing" visual signal in which a flexible first indicator element 118 in the form of a flexible container or tray 200 that is formed from or includes a flexible foam or plastic 202 on a skin contacting side 204. A relatively rigid second indicator element 120 in the form of a clear plate or disk 206 is configured to cover or seal with the flexible container or tray 200 (that includes an indicia 208) thereby enclosing a generally opaque medium 210 such as a colored water, colored liquid, liquid suspension, gel or other material. Alternatively, the structure shown in FIGS. 7A to 7D may be inverted so a relatively rigid first indicator element 118 may be a hard disk (not shown) that also includes an indicia and a flexible second indicator element 120 may be a separate flexible container or tray (not shown) formed from or includes a clear flexible plastic that seals with the relatively rigid first indicator element 118 to enclose a generally opaque medium 210 such as a colored liquid or gel. As the stoma length increases, the flexible indicator element compresses to reveal a visual cue in the form of indicia 208 signaling the indicator is under pressure and the retainer 114 may require readjustment.

Figure 7A:
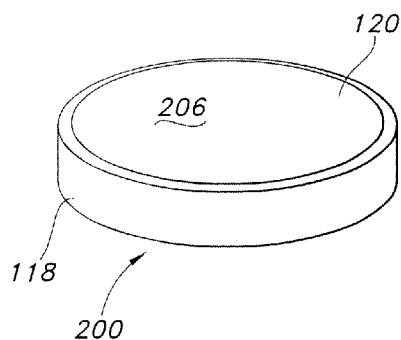
FIGS. 7A and 7C are perspective views illustrations a detail of another exemplary stoma length indicator assembly.
Figure 7B:
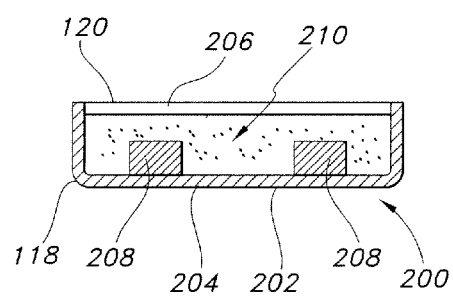
FIGS. 7B and 7D are side cross-section views illustrating a detail of yet another exemplary stoma length indicator assembly.
Figure 7C:
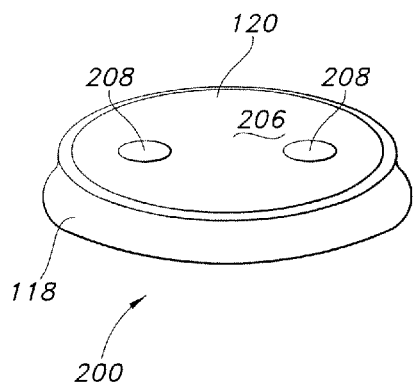
Figure 7D:
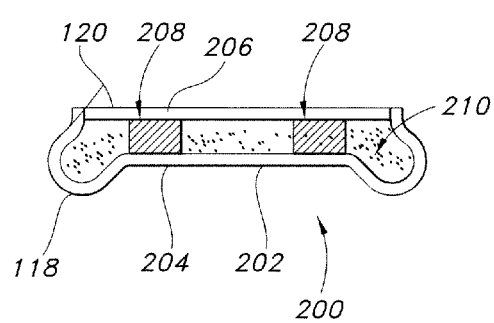

As a non-limiting example, a relatively opaque medium 210 (e.g., a colored liquid or gel) may be enclosed or sealed in a space defined between a relatively rigid clear plate or disk 206 (e.g., upper piece) and a flexible first indicator element 118 (e.g., bottom piece) which may be a clear, flexible plastic tray or container 200. The first indicator element 118 (e.g., bottom piece) is formed such that it has raised or attached indicia 208 such as graphics on an inside surface as illustrated in FIG. 7B. The opaque medium 210 contained between the first indicator element 118 and the second indicator element 120 must be sufficiently flowable or elastic such that under compression, it is displaced as the first indicator element 118 is deformed, yet still will revert to its uncompressed form after the compression force is removed and the first indicator element returns to its uncompressed form. Compression causes the indicia 208 of the first indicator element 118 to become visible through the opaque medium 210 and provide a signal that is visible through the clear plate or disk 206 that is the second indicator element 120. Desirably, the indicia are a color that contrasts against the opaque medium.

Exemplary indicators may also be constructed in which light scattering differences within very soft, flexible materials indicate a change in the length of the stoma tract. For example, a second indicator element 120 formed of a translucent material, or a relatively transparent material incorporating a patterned or textured surface (which materials may have a first color) may be located directly above a first indicator element 118 that may be in the form of a disk or similar structure having a different color or deeper shade of the same color or dark-colored or patterned surface. Upon compression (e.g., movement between the first and second indicator elements 118, 120 which compresses the soft polymer), the different color or deeper shade of the same color or dark-colored or patterned surface becomes visible through the translucent material, or a relatively transparent material incorporating a patterned or textured surface (which materials may have a first color) to effectively change its color and provide a signal indicating a change in stoma length.

Figure 8:
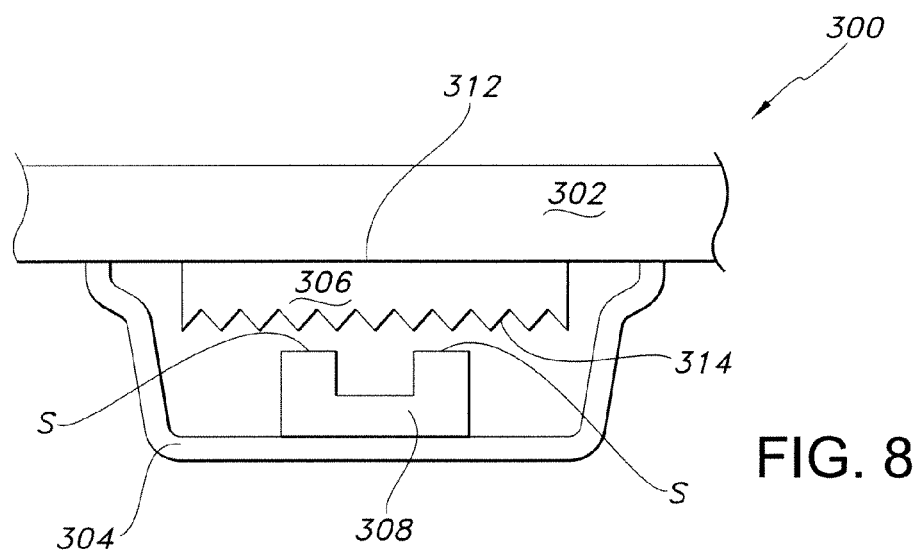
FIG. 8 is a side cross-section view illustrating a detail of an exemplary stoma length indicator assembly.

FIGS. 8 to 12 illustrate other exemplary embodiments of indicators that involve light scattering differences. Referring now to FIG. 8 of the drawings, there is illustrated an exemplary indicator design that is configured to use pressure against flexible portions of the indicator to generate a visible image. More particularly, the indicator design can be configured to control how incident light is reflected from a surface through the use of a diffusor. FIG. 8 is a side, cross-sectional illustration of an indicator 300 (which may be a sub-assembly) that includes a transparent or translucent plate 302 that functions as a second indicator element 120. The indicator includes a first indicator element 118 in the form of a deformable foot 304. The assembly also includes an indicator diffusor 306. The assembly also includes an image block 308 which may be a shape block or similar article that is configured to provide an image 310 when it becomes visible through the diffusor 306 and transparent or translucent plate 302.

Figure 9:
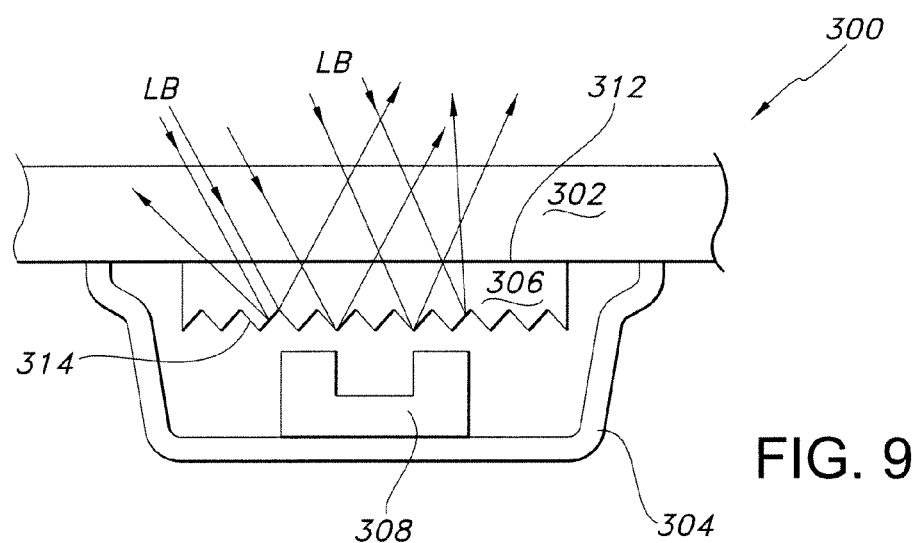
FIG. 9 is a side cross-section view illustrating a detail of an exemplary stoma length indicator assembly.

The indicator diffusor 306 is a transparent material that has a first surface 312 and a second surface 314. The first surface 312 facing out toward a viewer is flat and smooth. Referring now to FIG. 9, incident light beams "LB" will remain relatively unscattered or parallel after passing through the first surface 312 into the diffusor 306. The second surface 314 facing the image block 308 has a surface roughness or texture which may be either random or a patterned such that parallel beams of light "LB" traveling from inside the diffusor plate will generally reflect or refract from the diffusor plate surface in non-parallel beams or scattered which effectively diffuses the light. In addition, it is thought that the difference between the index of refraction of the diffusor 306 and that of the air (or the medium in the space between the image block and the second surface 314 of the diffusor) also scatters the light such that it is effectively diffused.

As illustrated in FIG. 9, when a compressive force on the deformable foot 304 is so low that the image block 308 is not contacting the second surface 314 of the diffusor 306, any light that reaches the second surface 314 will be scattered in a way that it is relatively diffused. As a result, the first surface 312 of the diffusor 306 will have a uniform appearance and no image of the image bock 308 will be visible through the transparent or translucent plate 302. That is, a large portion of the light reaching the second surface 314 of the diffusor 306 (which contains a "diffusion" texture) will be reflected in some random orientation due to the texture on the second surface and refraction.

Figure 10:
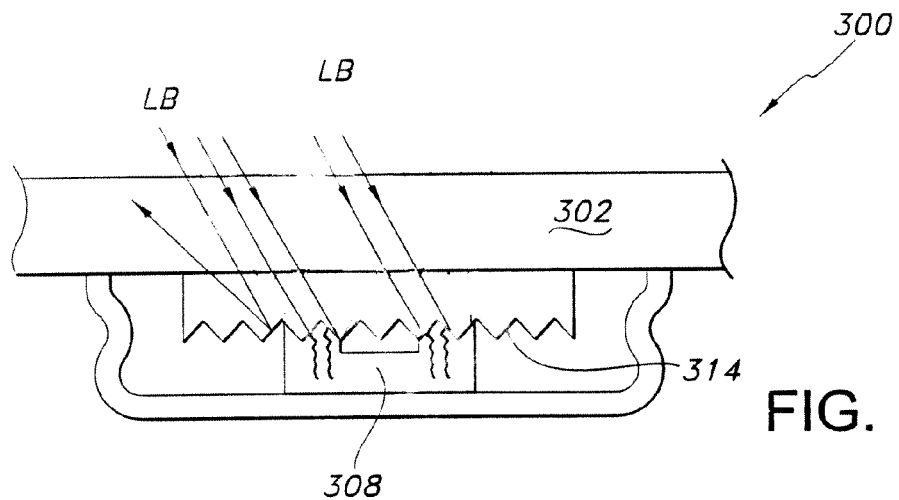
FIG. 10 is a side cross-section view illustrating a detail of an exemplary stoma length indicator assembly.
Figure 11:
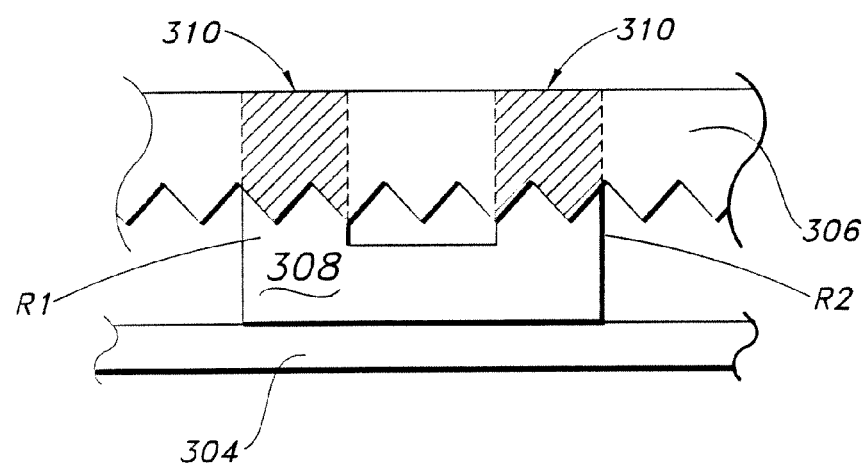
FIG. 11 is a side cross-section view illustrating a detail of an exemplary stoma length indicator assembly.

Referring to FIG. 10, when the compressive force on the deformable foot 304 is high enough that the image block 308 is able to make contact with the second surface 314 of the diffusor 306, the low modulus material of the image block 308 deforms into the texture at the second surface 314 of the diffusor 306. As illustrated in FIG. 10, the contact between the image block 308 and the second surface 314 of the diffusor 306 alters the diffusion of light due to minimization of index of refraction differences the light encounters. That is, the difference between the index of refraction of the diffusor 306 and that of the air (or the medium in the space between the image block and the second surface 314 of the diffusor) is different from the difference between the index of refraction of the diffusor 306 and that of the material of the image block 308 such that more light is transmitted through the second surface 314 of the diffusor rather than reflected or scattered. This transmitted light will not be reflected back through the diffusor 306 and transparent or translucent plate 302 toward a viewer. As seen in FIG. 11, the two locations "R1" and "R2" on the second surface 314 of the diffusor 306 that are in contact with the shape block 308 will generally appear darker than the surrounding diffusor material. This increased contrast makes the image 310 of the shape block 308 visible to the viewer through the transparent or translucent plate 302.

According to an aspect of the invention, the indicator block 308 is made from a low modulus material. The image block 308 is formed in a way that the surface "S" of the block 308 facing the diffusor 306 has a specified shape. The shape of the block 308 is used to define the indicated image 310. One technique for defining the indicator block shape is for the indicator block 308 to have a cross-section that defines the image 310. For example, an image block 308 in the form of a cylinder would have a surface "S" facing the diffusor 306 having a circular cross-section that would create an image 310 of a circle. It is contemplated that an image block 308 may provide one or more surfaces "S" facing the diffusor 306 having one or more shapes (including alphanumeric characters) that would create one or more images 310.

FIGS. 12A to 12C illustrate another technique for generating an image in response to pressure or displacement. Referring to FIG. 12A, an image block 308 may be a binary or multi-component image block. For example, a binary image may be composed of a "base" image block 330 formed of a relatively non-deformable material and a relatively deformable "upper" image 332 in the form of a cylinder which is positioned on top of that base image block 330 in the general direction of the arrow "A". When under no compression load, no image is visible through the image plane "PL" as generally represented in FIG. 12B. At some controlled load, an image 310 becomes visible on the image plane PL as illustrated in FIG. 12C.

Figure 13:
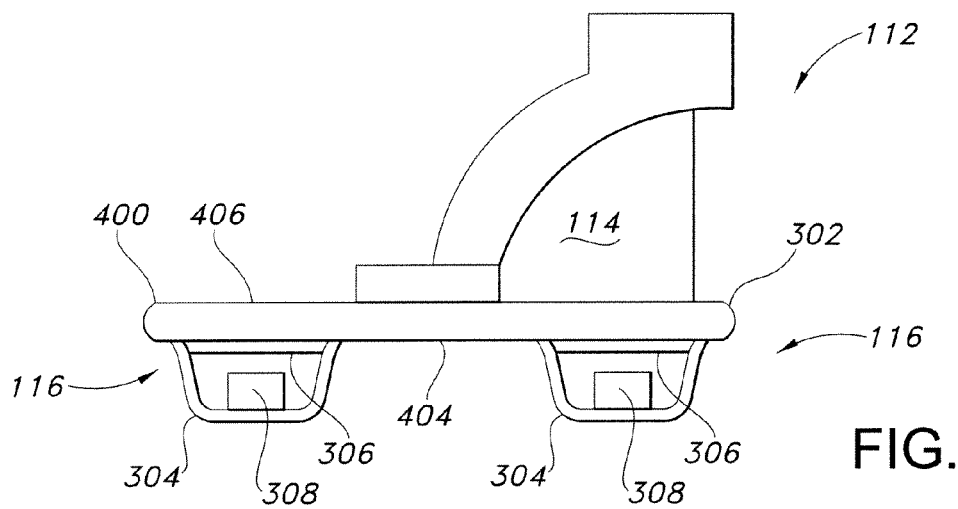
FIG. 13 is a side cross-section view illustrating an exemplary stoma length indicator assembly.
Figure 14:
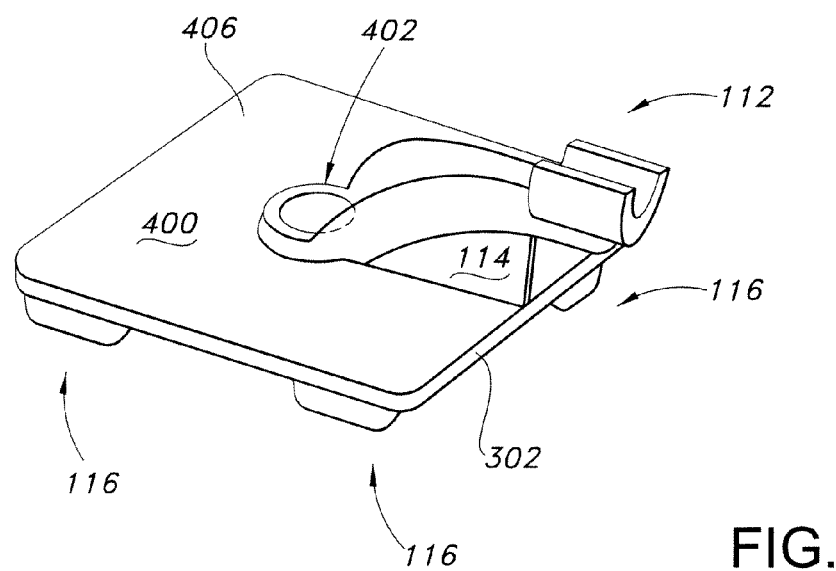
FIG. 14 is a perspective view illustrating an exemplary stoma length indicator assembly shown in FIG. 13.
Figure 15:
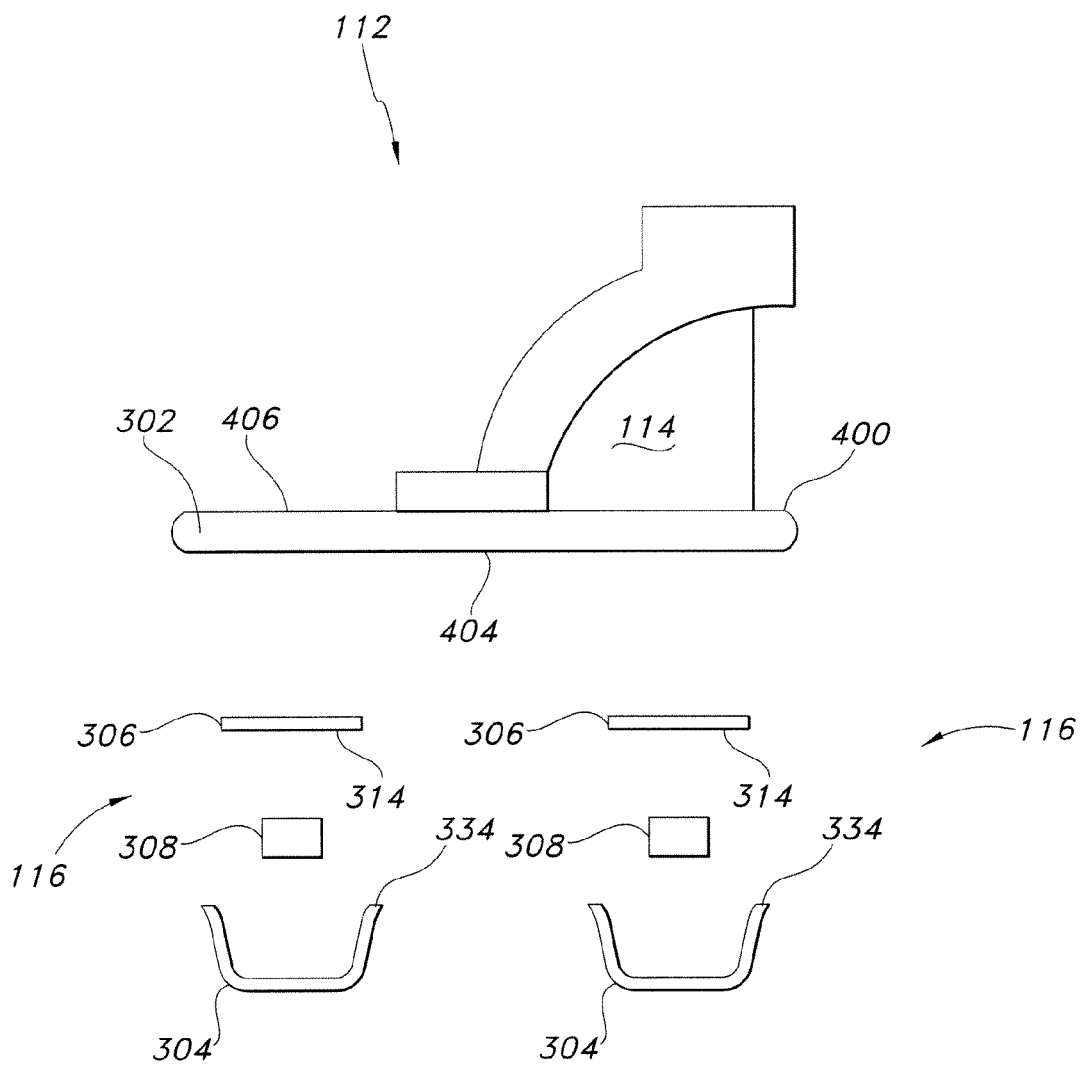
FIG. 15 is an exploded cross-section view illustrating an exemplary stoma length indicator assembly shown in FIG. 13.

Referring to FIGS. 13 to 15, there is illustrated in side, cross-sectional view (FIG. 13), perspective view (FIG. 14) and exploded side view (FIG. 15), an exemplary and non-limiting embodiment in which the image block 308 is attached to the inner surface of the deformable foot 304 as generally described above but employed in an indicator assembly 112 in which a second retainer 114 has a 90 degree bend to accommodate a low-profile configuration. The upper edge 334 of the deformable foot 304 is attached to the base of an indicator 116. When the indicator 116 is pressed down with some force the foot 304 deforms allowing the image block 308 to contact the diffusor 306. The shape and material of the deformable foot 304 and the size of the image block 308 will determine the force required to cause the image block 308 to contact the diffusor 306.

The indicator 116 will show an image when the image block 308 is in contact with the diffusor 306. This is designed to happen when the distance between the upper surface "S" of the image block 308 and the second surface 314 of the diffusor 306 is smaller. This occurs when there is a compressive force between the two surfaces that brings the upper surface "S" of the image block 308 (usually through deformation of the deformable foot 304) and the second surface 314 of the diffusor 306 closer together.

The indicator assembly 116 may be joined or integrated with to a primary support base 400 which can serve as the transparent or translucent plate 302. This base 400 can be a variety of shapes and sizes and should define a hole or slot 402 for the feeding tube to fit through. An indicator sub-assembly 116 (or plurality of sub-assemblies) can be located on the bottom side 404 (side closest to the skin) of the base 400 as illustrated in FIGS. 13 to 15.

Figure 16:
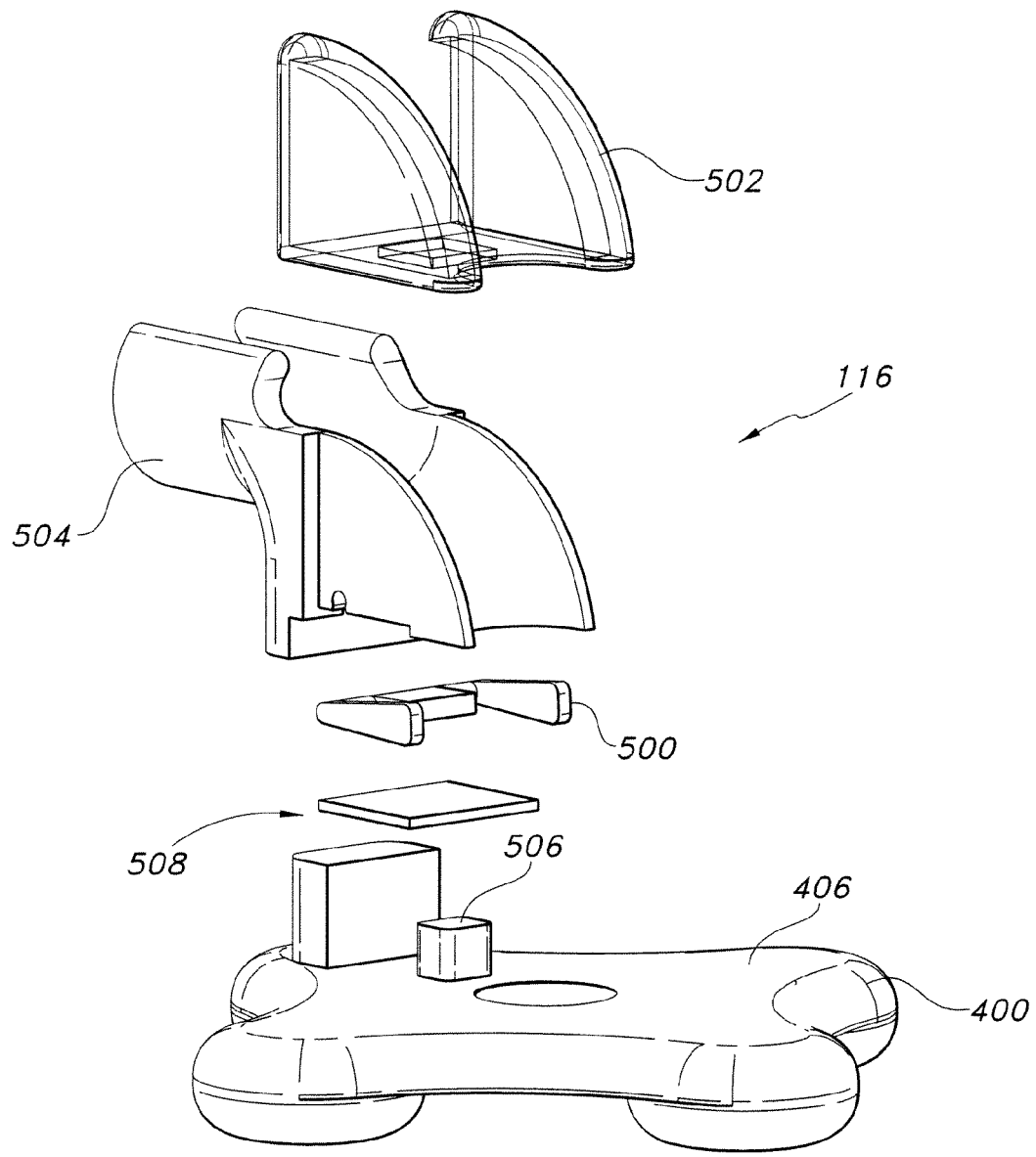
FIG. 16 is an exploded perspective view illustrating an exemplary stoma length indicator assembly.

In another embodiment of the invention, the indicator 116 may be located on the top side 406 of the base 400 as generally illustrated in FIG. 16. In this configuration, an indicator lever 500 is visible in a window 502 that sandwiches both sides of a 90 degree bend 504. The base 400 in this embodiment is very flexible and will readily deform causing a post 506 to deflect into a flexible sheet 508 that causes the indicator lever 500 to change from an initial position (e.g., horizontal) to a second position (e.g., vertical) to signal a change in the length of the stoma.

The base can be made to have various levels of hardness, ranging from very soft and flexible to completely rigid. For example, useful materials of different hardness ratings include (but are not limited to): Water Clear-565 polyurethane (BJB, Hardness 65 Shore A) and Shincor-KE-1950-50 silicone (Shin-Etsu, Hardness 50 Shore A). Desirably, the base may be made with a transparent or translucent material in order for the indicator to be visible. In configurations in which the indicator sub-assembly is on the top side of the primary support base (e.g., FIG. 16), the base should be a soft material, preferably equal to or softer than human tissue. The primary support base in such configuration (i.e., the indicator sub-assembly is on the top side of the primary support base) can range from transparent to completely opaque.

The indicator sub-assembly also desirably contains a surface component that may be described as a frosted surface or patterned surface of a particular roughness located between the indicator and the field of view for the user. This surface can either be an integral part of the base (via surface modification to injection molding tooling, for example) or a separate, discreet piece. One specific example of a separate surface component is a polyester film cut to an appropriate shape.

The indicator sub-assembly may further include an indicator shell corresponding to the locations of indication. This piece can be any size or shape and can be placed at a variety of locations on the base. As noted above, multiple indicator sub-assemblies can be incorporated into a single device. It is thought that the material selected for the shell of the sub-assembly (or sub-assemblies) depends on the location of the sub-assembly. For devices in which the location of indication (i.e., the location of the sub-assembly) is spaced away from the primary center axis, the indicator shell material hardness should be less than the hardness of the base structure. As an example, bases constructed with 50 Shore A and 65 Shore A materials may be combined with indicator structures (e.g., shells of the indicator sub-assembly) that may be made with both a 10 Shore A and a 15 Shore A material (Smooth-On MoldMax10T Silicone and Smooth-On MoldMax 15T Silicone, respectively). As a different example, when the indicator sub-assembly (or sub-assemblies) is located on the top side of the base, the indicator shell should be a rigid material to provide the indicator a rigid surface to contact upon activation.

The indicator sub-assembly also contains a colored indicator component. This component may be made of a soft material and have different sizes and shapes. An embossed symbol, including letters, numbers, symbols, etc., on the top surface can be incorporated to provide a signal. The colored indicator component can be different colors and should be made with a material softer than the indicator shell. Exemplary materials include silicone materials with a Shore 00 hardness of between 10 and 30. In the state in which the indicator component is not providing a signal, the top surface of the colored indicator component should be positioned offset from the frosted surface. That gap distance, in addition to material selection, determines the distance and force required to activate the indicator. Once activated, the top surface of the colored indicator makes physical contact with the frosted surface component and the embossed feature becomes visible to the user.

All of these discrete components can be assembled and joined together with several common adhesives, including cyanoacrylate. Other silicone adhesives such as 732 Multi-Purpose Sealant (Dow Corning) are effective as well.

The present invention also encompasses a positioning system for a retainer of a non-vascular catheter device having a catheter tube, an indwelling first retainer which is deployed within a lumen of the body by insertion through a stoma, a second retainer, e.g. a base deployed outside the human body, and an indicator. The positioning system includes the general structure described above in which a first retainer is fixedly attached to a catheter tube, the first retainer being an indwelling retainer for deployment within a lumen of the body. The second retainer is releasably secured to the tube such that the location of second retainer on the tube may be changed. An indicator as generally described above is located on the tube between the first retainer and the second retainer. The indicator is deployed at a surface of the skin of the patient to provide a placement signal. In this regard, a placement signal is provided by advancing the second retainer toward the first retainer so the indicator generates a placement signal and then retracting the second retainer away from the first retainer so the indicator no longer generates a placement signal. At this point, the second retainer may be releasably secured to the tube without providing excess pressure on the stoma.

Another aspect of the invention encompasses a repositionable indicator system for a catheter tube having a base deployed outside the human body and an indwelling retainer which is deployed within a lumen of the body by insertion through a stoma. The repositionable indicator system has the structure generally described above and includes an external retainer incorporating a releasable lock to releasably secure the retainer on a catheter tube outside the human body. The system also includes an indicator as generally described above which is located on the tube, the indicator being configured to be positioned between the skin of a patient and the retainer such that the indicator provides a signal in response to a force applied to the indicator between the skin and the external retainer.

Yet another aspect of the invention encompasses a method for positioning an external retainer of a catheter device having a catheter tube, a base as a second retainer deployed outside the human body, an indwelling retainer which is deployed within a lumen of the body by insertion through a stoma, and an indicator. The method generally utilizes the indicators and assemblies describe above and includes the steps of: (a) inserting a portion of a catheter tube (e.g., enteral feeding tube, jejunal tube, peritoneal drainage tube or the like) incorporating part of the indicator assembly as generally described above through a stoma to deploy a first retainer within a lumen of the body, for example, a gastric lumen; (b) advancing a second retainer, releasably securable to the tube and deployed outside the human body, towards the first retainer until an indicator deployed at a surface of the skin of the patient provides a placement signal; (c) retracting the second retainer away from the first retainer until the indicator no longer provides a placement signal; and (d) releasably securing the second retainer to the tube.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. An indicator assembly for use with an indwelling non-vascular catheter device having a base for deployment outside a human body and an indwelling retainer for deployment within a lumen or cavity of the human body by insertion through a stoma, the assembly comprising:
   a first retainer secured to a catheter tube, the first retainer being an indwelling retainer for deployment within the human body;
   a second retainer secured to the catheter tube, the second retainer being an external retainer for deployment outside the human body; and
   an indicator configured to be located outside the human body on the catheter tube between the first retainer and the second retainer, the indicator including an indicia,
   wherein the first retainer and the second retainer are configured to maintain substantially a same position with respect to each other on the catheter tube and the indicator is configured to reveal the indicia to provide a signal indicating a change in position with respect to either the first or the second retainer thereby indicating a change in a length of a stoma,
   wherein the indicator includes at least a first indicator element and a second indicator element, and
   wherein at least one of the indicator elements is configured to be movable or deformable with respect to the other of the indicator elements and the signal provided by the indicator is a visual signal or a tactile signal.

2. The indicator assembly of claim 1, wherein the first retainer is configured to be positioned in a non-vascular lumen or cavity of a patient; the indicator is configured to have a skin-contacting side; and the second retainer is configured to be positioned above the indicator.

3. The indicator assembly of claim 1, wherein the second retainer is releasably secured to the catheter tube such that a location of the second retainer on the catheter tube may be changed.

4. The indicator assembly of claim wherein at least one of the indicator elements is affixed to the catheter tube.

5. The indicator assembly of claim 1, wherein the indwelling non-vascular catheter device is selected from an enteral feeding tube, a jejunal feeding tube, and a peritoneal drainage tube.

6. An indicator assembly for use with a non-vascular catheter device having a base for deployment outside a human body and an indwelling retainer for deployment within a lumen or cavity of the human body by insertion through a stoma, the assembly comprising:
   a first retainer secured to a catheter tube, the first retainer being an indwelling retainer which is configured for deployment within a non-vascular lumen or cavity of the human body, the catheter tube defining a longitudinal axis;
   a second retainer secured to the catheter tube, the second retainer being an external retainer for deployment outside the human body; and
   an indicator secured to the catheter tube such that it is configured to be located outside the human body, the indicator comprising at least a first indicator element and a second indicator element,
   wherein the first retainer and the second retainer are configured to maintain substantially the same position with respect to each other on the catheter tube and at least the first indicator element is configured to translate axial movement along the longitudinal axis into rotational movement of a component with respect to at least the second indicator element to signal a change in position of the indicator with respect to the first retainer thereby indicating a change in a length of a stoma.

7. The indicator assembly of claim 6, wherein the first retainer is configured to be positioned in a lumen or cavity of a patient and the indicator is configured to have a skin-contacting side.

8. The indicator assembly of claim 6, wherein at least one of the indicator elements is releasably secured to the catheter tube such that a location of the indicator on the catheter tube may be changed.

9. The indicator assembly of claim 6, wherein the non-vascular catheter device is selected from an enteral feeding tube, a jejunal feeding tube, and a peritoneal drainage tube.

10. A positioning system for a retainer of a non-vascular catheter device having a base for deployment outside a human body and an indwelling retainer for deployment within a lumen or cavity of the human body by insertion through a stoma, the positioning system comprising:
    a first retainer fixedly attached to a catheter tube, the first retainer being an indwelling retainer for deployment within a non-vascular lumen or cavity of the human body;
    a second retainer releasably secured to the catheter tube such that a location of the second retainer on the catheter tube may be changed, the second retainer being an external retainer for deployment outside the human body; and
    an indicator located on the catheter tube between the first retainer and the second retainer, the indicator having a skin-contacting side and an indicia to provide a placement signal,
    wherein advancing the second retainer toward the first retainer generates the placement signal and then retracting the second retainer away from the first retainer no longer generates the placement signal to provide a placement position for the second retainer such that the second retainer may be releasably secured to the catheter tube.

11. The positioning system of claim 10, wherein the placement signal is a visual signal or a tactile signal.

12. The positioning system of claim 10, wherein the non-vascular catheter device is selected from an enteral feeding tube, a jejunal feeding tube, and a peritoneal drainage tube.

13. A repositionable indicator system for a non-vascular catheter device having a base for deployment outside a human body and an indwelling retainer for deployment within a lumen or cavity of the human body by insertion through a stoma, the repositionable indicator system comprising:

an indwelling retainer that is configured to be positioned in a non-vascular lumen or cavity;

an external retainer configured to be positioned outside a human body, the external retainer releasably secured to a catheter tube; and an indicator located on the catheter tube and configured to be located outside the human body between skin of a patient and the external retainer, the indicator including an indicia, wherein the indicator includes at least a first indicator element and a second indicator element, wherein at least one of the indicator elements is configured to be movable or deformable with respect to the other of the indicator elements, and wherein the indicator provides a signal in response to a force applied to the indicator between the skin and the external retainer.

14. The repositionable indicator system of claim 13, wherein the signal is a visual signal or tactile signal.

15. The indicator assembly of claim 13, wherein the non-vascular catheter device is selected from an enteral feeding tube, a jejunal feeding tube, and a peritoneal drainage tube.

16. A method for positioning an external retainer of an indwelling non-vascular catheter device having a base for deployment outside a human body and an indwelling retainer for deployment within a lumen or cavity of the human body by insertion through a stoma, the method comprising the steps of:

inserting a portion of a catheter tube incorporating the indicator assembly of claim 1 through a stoma for deployment of the first retainer within a non-vascular lumen or cavity;

advancing the second retainer, releasably securable to the catheter tube and configured for deployment outside the human body, towards the first retainer until the indicator having a skin-contacting surface and the indicia provides a signal;

retracting the second retainer away from the first retainer until the indicator no longer provides the placement signal; and releasably securing the second retainer to the catheter tube.

17. The method of claim 16, wherein the non-vascular catheter device is selected from an enteral feeding tube, a jejunal feeding tube, and a peritoneal drainage tube.

18. The method of claim 17, wherein the non-vascular catheter device is an enteral feeding tube and the first retainer is configured to be positioned in a gastric lumen of a patient.

* * * * *